US006248190B1

(12) United States Patent
Stinson (10) Patent No.: US 6,248,190 B1
(45) Date of Patent: Jun. 19, 2001

(54) PROCESS OF MAKING COMPOSITE STENTS WITH GOLD ALLOY CORES

(75) Inventor: Jonathan S. Stinson, Plymouth, MN (US)

(73) Assignee: SciMed Life Systems, Inc., Plymouth, MN (US)

( * ) Notice: Subject to any disclaimer, the term of this patent is extended or adjusted under 35 U.S.C. 154(b) by 0 days.

(21) Appl. No.: 09/333,720

(22) Filed: Jun. 15, 1999

Related U.S. Application Data

(60) Provisional application No. 60/089,247, filed on Jun. 15, 1998.

(51) Int. Cl.[7] ....................................................... C22F 1/14
(52) U.S. Cl ............................. 148/519; 148/527; 148/678
(58) Field of Search ................................... 148/516, 519, 148/521, 527, 678

(56) References Cited

U.S. PATENT DOCUMENTS 5,630,840 * 5/1997 Mayer, I. ................................. 623/1
5,679,470 * 10/1997 Mayer, II. ............................ 148/527
5,858,556 * 1/1999 Eckert et al. ........................ 148/521

* cited by examiner

Primary Examiner—George Wyszomierski
(74) Attorney, Agent, or Firm—Larkin, Hoffman, Daly & Lindgren, Ltd.; Frederick W. Niebuhr, Esq.

(57) ABSTRACT

A body compatible stent is formed of multiple filaments arranged in two sets of oppositely directed helical windings interwoven with one another in a braided configuration. Each of the filaments is a composite including a central core (24) and a case (26) surrounding the core (24). The core is formed of a radiopaque and relatively ductile material, in particular gold or a gold alloy. The outer case (26) is formed of a relatively resilient material, e.g. a cobalt/chromium based alloy. Favorable mechanical characteristics of the stent are determined by the case (26), while the core (24) enables in vivo imaging of the stent. The composite filaments are formed by a drawn filled tubing process in which the core (24) is inserted into a tubular case (26) of a diameter substantially more than the intended final filament diameter. The composite filament is cold-worked in several steps to reduce its diameter, and annealed between successive cold-working steps. After the final cold working step, the composite filament is formed into the desired shape and age hardened.

32 Claims, 2 Drawing Sheets

PROCESS OF MAKING COMPOSITE STENTS WITH GOLD ALLOY CORES

This application claims the benefit of U.S. Provisional Application No. 60/089,247 entitled Process of Making Composite Stents with Gold Alloy Cores, filed Jun. 15, 1998.

BACKGROUND OF THE INVENTION

The present invention relates to the manufacture of body implantable medical devices, and more particularly to making stents and other prostheses configured for high radio-opacity as well as favorable mechanical characteristics.

Several prostheses, typically of latticework or open frame construction, have been developed for a variety of medical applications, e.g. intravascular stents for treating stenosis, prostheses for maintaining openings in the urinary tracts, biliary prostheses, esophageal stents, renal stents, and vena cava filters to counter thrombosis. One particularly well accepted device is a self-expanding mesh stent disclosed in U.S. Pat. No. 4,655,771 (Wallsten). The stent is a flexible tubular braided structure formed of helically wound thread elements.

Alternatively, stents and other prostheses can be expandable by plastic deformation, usually by expanding a dilation balloon surrounded by the prosthesis. For example, U.S. Pat. No. 4,733,665 (Palmaz) discloses an intraluminal graft constructed of stainless steel strands, either woven or welded at their intersections with silver.

Regardless of whether the prosthesis is self-expanding or plastically expanded, accurate placement of the prosthesis is important to its effective performance. Accordingly, there is a need to visually perceive the prosthesis as it is being placed within a blood vessel or other body cavity. Further, it is advantageous to visually locate and inspect a previously deployed prosthesis.

Fluoroscopy is the prevailing technique for such visualization, and it requires radio-opacity of the materials to be imaged. The preferred structural materials for pros-thesis construction, e.g. stainless steels and cobalt-based alloys, are not highly radiopaque in the thin-section sizes of stent wires. Consequently, endoluminal prostheses con-structed of these materials do not lend themselves well to fluoroscopic imaging.

A particularly advantageous stent construction, in terms of providing radio-opacity and mechanical integrity, is dis-closed in U.S. Pat. No. 5,630,840 (Mayer). The Mayer device discloses a stent formed of multiple filaments, preferably arranged in at least two sets of oppositely directed helical windings interwoven with one another in a braided configuration. Each filament is a composite including a core surrounded by a case. Preferably, the core provides the desired radio-opacity, while the case governs mechanical behavior. Suitable core materials include tantalum and a platinum nickel alloy. Suitable case materials include certain alloys composed primarily of cobalt and chromium, e.g. sold under the brand names Elgiloy and MP35N.

Although such composite filaments provide the desire d mechanic al characteristics and good fluoroscopic visibility, the primarily platinum core is expensive.

Accordingly, one object of the present invention is to provide a process for making composite filament for use in stents and other body insertable medical devices, that is less expensive than composite filaments with primarily platinum cores.

Tantalum cores are less expensive than platinum cores, but require special processing. During reduction of a tantalum billet or bar to a rod or wire for use as the core, the material is aninealed to enhance its formability. Annealing usually occurs in a hydrogen atmosphere to prevent oxidation of the tantalum. Hydrogen is absorbed by the tantalum during annealing, and must later be removed by a vacuum treatment to avoid hydrogen concent rations in the metal. During the age hardening stage of composite filament construction, any residual hydrogen in the tantalum core can lead to hydrogen outgassing, increasing the time needed to achieve satisfactory vacuum levels within the age hardening furnace for protecting the case material from oxidation.

Accordingly, another object of the present invention is to provide a process for making composite filaments in a manner that avoids hydrogen outgassing during the processing of filaments or stents and other devices composed of the composite filaments.

A further object of the invention is to provide a composite filament fabrication process incorporating cold-working stages and annealing stages performed under conditions more suitable for filaments having cores with melting temperatures lower than those of tantalum and platinum.

Another object is to provide a process for fabricating composite filaments for devices that, when inserted or implanted in the body, are less likely to interfere with magnetic resonance imaging of tissue adjacent and surrounding the devices.

Yet another object of the invention is to provide a process particularly well suited to fabricating a composite filament having a gold or gold alloy core.

SUMMARY OF THE INVENTION

To achieve these and other objects, there is provided a process for manufacturing a body insertable composite filament. The process includes the following steps:

a. providing (i) an elongate core substantially uniform in lateral cross-section and comprising a gold alloy containing from about 60 weight percent to about 99 weight percent gold, and having a melting temperature above 1600° F. (870° C.), and (ii) an elongate tubular case substantially uniform in lateral cross-section and formed of a metal;

b. inserting the core into the case to form an elongate composite filament in which the case surrounds the core;

c. cold working the composite filament to reduce its outside diameter;

d. annealing the composite filament after cold working, at an average annealing temperature of at most 2000 degrees F. (1093 degrees C) and at a maximum annealing temperature less than a melting point of the core, to substantially remove strain hardening induced by the cold working;

e. cold working the annealed composite filament in a final cold-working stage, and then forming the cold-worked composite filament into an intended shape; and f. while maintaining the cold-worked composite filament in the intended shape, age hardening the case.

The cold-working step can include drawing the composite filament serially through several dies, with each die plastically deforming the composite filament to reduce the outside diameter. Whenever a stage including one or more cold working dies has reduced the cross-sectional area by at least 15 percent and the ductility of the composite filament is sufficiently low (i.e., less than about 10 percent tensile elongation) to raise a risk of fracture during further cold-working, an annealing step should be performed before any further cold-working. During each annealing step, the composite filament is heated to a temperature in the range of about 1400–2000 degrees F. (760 degrees C. to 1093 degrees C.) for a period depending on the filament diameter, typically in the range of several seconds to several minutes.

In an alternative version of the process, the initial outside diameter of the composite structure (billet) typically is at least fifty millimeters (about two inches) in diameter. Then, before cold-working, the composite filament is subjected to temperatures in the annealing range while the outside diameter is substantially reduced, either by swaging or by pulltrusion, in successive increments until the outside diameter is at most about 6 millimeters (0.25 inches). The resulting filament is processed as before, in alternative cold-working and annealing stages.

Further according to the process, the composite filament can be severed into a plurality of strands. Then, the strands are arranged in two oppositely directed sets of parallel helical windings about a cylindrical form, with the strands intertwined in a braided configuration to form multiple intersections. Then, while the strands are maintained in a predetermined uniform tension, they are heated to a temperature in the range of about 500–700° C. (930–1290° F.), more preferably about 550° C. (1020° F.), for a time sufficient to age harden the case material of the helical windings.

The process can be employed to form a body compatible device comprising an elongate filament substantially uniform in lateral cross-section over its length and including an elongate cylindrical core and an elongate tubular case surrounding the core. The case is constructed of a material having a yield strength (0.2% offset) of at least 300,000 psi. The core is constructed of gold or a gold alloy. In a highly preferred version of the invention, the case is constructed of a cobalt-based alloy, e.g. as available under the brand names "Elgiloy", "Phynox" and "MP35N". The "Elgiloy" and "Phynox" alloys contain cobalt, chromium, nickel, and molybdenum, along with iron.

In accordance with another preferred version of the invention, the process is used to form a filament with a case constructed of a more ductile material, e.g. tantalum or annealed stainless steel. These materials provide a case with a moderately high yield strength and high ductility, so that stents or other devices formed with the composite filament can be radially expanded plastically, e.g. by expanding a balloon along a distal end region of a catheter that also carries the device, in surrounding relation to the balloon.

According to another aspect of the invention, there is provided a process for manufacturing a body insertable composite filament with a gold alloy core, including:

a. providing an elongate core substantially uniform in lateral cross-section and consisting essentially of gold, and an elongate tubular case substantially uniform in lateral cross-section and formed of a metal;

b. inserting the core into the case to form an elongate composite filament in which the case surrounds the core;

c. cold working the composite filament to reduce its outside diameter;

d. annealing the composite filament after cold working, at an average annealing temperature of 1400–1900 degrees F. (760–1038 degrees C.) and at a maximum annealing temperature below a melting point of the core, to substantially remove strain hardening and other stresses induced by the cold working;

e. cold working the annealed composite filament in a final cold-working stage, thereby reducing a lateral cross-sectional area of the composite filament by about 30–70 percent; and f. after the final cold-working stage, age hardening the case.

Composite filaments according to the present invention, whether employing cores of gold or gold alloys, reduce the cost of filaments as compared to composite filaments employing platinum or primarily platinum cores. Conversion of the gold or gold alloy billet or bar to a rod or wire suitable as a core can include an annealing process in an air atmosphere.

Alloys that consist primarily of gold are well suited for providing the requisite radio-opacity. The linear attenuation co-efficient of gold at 50 KeV is 140.12 cm$^{-1}$, as compared to 94.95 cm$^{-1}$ at 50 KeV for tantalum, and 149.08 cm$^{-1}$ at 50 KeV for platinum. The atomic weight of gold is 196.97, as compared 180.95 for tantalum and 195.08 for platinum. The atomic numbers of gold, tantalum and platinum are 79, 73 and 78, respectively. The density of gold is 19.32 grams per cubic cm (g/cc), as compared to 16.65 g/cc for tantalum, and 21.45 g/cc for platinum.

Accordingly, composite filaments employing gold alloy cores compare well with such filaments with tantalum or platinum cores, in terms of visibility under fluoroscopic imaging and utility in connection with other imaging techniques.

Further, magnetic resonance imaging of body tissue adjacent an implanted or deployed device is facilitated when the device is composed of composite filaments with gold or gold alloy cores. Magnetic resonance (MR) scanners produce magnetic field gradients for analysis of the magnetic responses of constituents of the body. Small variations in magnetic susceptibility between normal and abnormal tissues can produce atypical images that indicate possible damaged or diseased areas. Typical metallic implants are considerably more magnetizable than body tissue, and consequently provide a strong response to the magnetic field, tending to obscure the comparatively subdued responses of the adjacent tissue.

Gold and gold alloy core materials, as compared to platinum and tantalum, have magnetic susceptibility much closer to that of body tissue. In particular, gold exhibits a magnetic susceptibility of $-34 \times 10^6$ cgs, much closer to the magnetic susceptibility of human tissues ($-11.0$ to $-7.0 \times 10^6$ cgs) then either platinum or tantalum, which have susceptibilities well over $100 \times 10^6$ cgs. As a result, devices composed of gold or gold alloy core filaments are less likely to interfere with or obscure the results of magnetic field imaging of adjacent tissue.

While disclosed herein primarily in connection with a radially self-expanding stent, the composite filaments can be employed in constructing other implantable medical devices, e.g. vena cava filters, blood filters and thrombosis coils. Thus, in accordance with the present invention there is provided a body compatible prosthesis which, despite being sufficiently small for placement within blood vessels and other body cavities, has sufficient radio-opacity for fluoroscopic imaging based on the prosthesis materials themselves.

IN THE DRAWINGS

For a further understanding of the above and other features and advantages, reference is made to the following detailed description and to the drawings, in which.

DETAILED DESCRIPTION OF THE PREFERRED EMBODIMENTS

Figure 1:
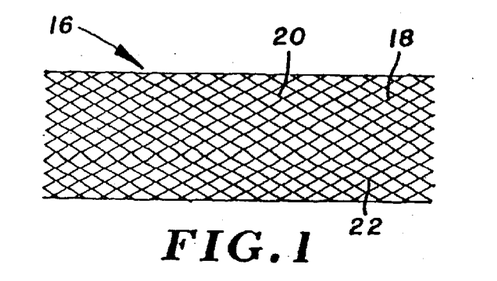
FIG. 1 is a side elevation of a self-expanding stent constructed according to the present invention.
Figure 2:
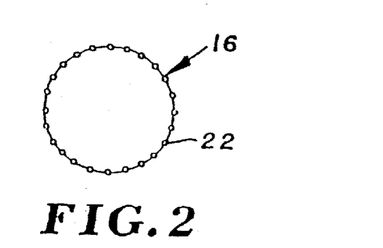
FIG. 2 is an end elevational view of the stent.

Turning now to the drawings, there is shown in FIGS. 1 and 2 a body implantable prosthesis 16, frequently referred to as a stent. Stent 16 is of open mesh or weave construction, consisting of two sets of oppositely directed, parallel and spaced apart helically wound strands or filaments indicated at 18 and 20, respectively. The sets of strands are interwoven in an over and under braided configuration to form multiple intersections, one of which is indicated at 22.

Stent 16 is illustrated in its relaxed state, i.e. in the configuration it assumes when subject to no external stresses. The filaments or strands of stent 16 are resilient, permitting a radial compression of the stent into a reduced-radius, extended-length configuration suitable for transluminal delivery of the stent to the intended placement site. As a typical example, stent 16 can have a diameter of about ten millimeters in the relaxed state, and is elastically compressed to a diameter of about 2 millimeters (0.08 inches) and an axial length of about twice the axial length of the relaxed stent. However, different applications call for different diameters. Further, it is well known to predetermine the degree of axial elongation for a given radial compression, by selectively controlling the angle between the oppositely directed helical strands.

Inelastic open-weave prostheses, expandable for example by dilation balloons, provide an alternative to resilient prostheses. Resilient or self-expanding prostheses can be deployed without dilation balloons or other stent expanding means. Self-expanding stents can be preselected according to the diameter of the blood vessel or other intended fixation site. While deployment of resilient stents requires skill in stent positioning, inelastic prosthesis deployment requires the additional skill of carefully dilating the balloon to plastically expand the prosthesis to the appropriate diameter. The self-expanding stent remains at least slightly elastically compressed after fixation, and thus has a restoring force which facilitates acute fixation. By contrast, a plastically expanded stent relies on the restoring force of deformed tissue, or on hooks, barbs, or other independent fixation elements.

Accordingly, materials forming the strands for filaments in self-expanding stents must be strong and resilient, biocompatible, and resistant to fatigue and corrosion. Vascular applications require hemocompatibility as well. Several materials meet these needs, including stainless "spring" steels, and certain cobalt-based alloys: more particularly two alloys including cobalt, chromium, iron, nickel and molybdenum sold under the brand names "Elgiloy" (available from Carpenter Technology Corporation of Reading, Pennsylvania) and "Phynox" (available from Metal Imphy of Imphy, France), respectively. Another suitable cobalt-chromium alloy is available under the brand name "MP35N" from Carpenter Technology Corporation of Reading, Pa.

Further, it is advantageous to form a prosthesis with substantial open space to promote embedding of the stent into tissue, and fibrotic growth through the stent wall to enhance long-term fixation. A more open construction also enables substantial radial compression of the prosthesis for deployment. In a typical construction suitable for transluminal implantation, the filaments can have a diameter of about 0.1 millimeter (0.004 inches), with adjacent parallel filaments spaced apart from one another by about 1–2 millimeters (0.04–0.08 inches) when the stent is in the relaxed state.

Fluoroscopic imaging of a conventional open weave prosthesis is extremely difficult. Due to their minute diameters and the materials involved, the filaments exhibit a relatively poor contrast to body tissue for fluoroscopic imaging purposes. The filaments also require a high degree of spatial resolution in the imaging equipment involved. Thus, a stent recognizable on X-ray film may not be distinguishable for real time imaging, due to the relatively poor spatial resolution of the video monitor as compared to X-ray film.

Figure 3:
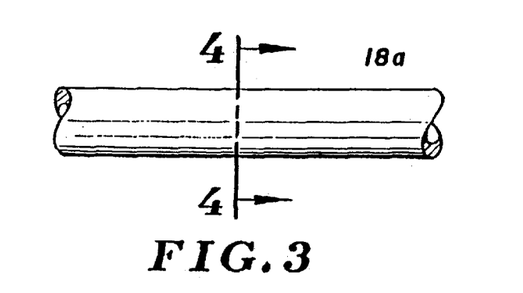
FIG. 3 is an enlarged partial view of one of the composite filaments forming the stent.
Figure 4:
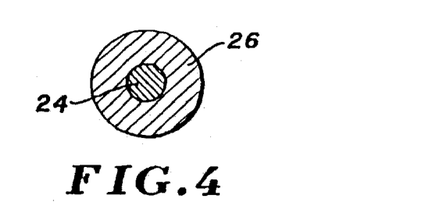
FIG. 4 is an enlarged sectional view taken along the line 4—4 in FIG. 3.

According to the present invention, however, prosthesis 16 is substantially more amenable to fluoroscopic imaging, due to the construction of strands 18 and 20. In particular, the strands cooperate to present a sufficiently radiopaque mass at the tangents of device 16 (parallel to the X-rays) for satisfactory real time imaging. As seen in FIGS. 3 and 4, a filament 18a of the prosthesis is of composite construction, with a radiopaque core 24 surrounded by and concentric with an annular resilient case 26. Core 24 is highly absorptive of X-rays, preferably having a linear attenuation coefficient of about 100 to about 150 $cm^{-1}$ at 50 KeV.

By contrast, case 26 is formed of a highly resilient material, preferably with a yield strength (0.2% offset) of at least 300,000 psi (2.07 GPa) and a modulus of elasticity of at least $25 \times 10^6$ psi (172.4 GPa). Consequently, the mechanical behavior of composite filament 18a in terms of elastic deformation in response to external stresses is, essentially, the behavior of case 26.

In one preferred embodiment, core 24 is formed of an AuAgCuPtPd gold alloy, and case 26 is formed of a cobalt-based alloy, more particularly Elgiloy (brand) alloy. The gold alloy, more particularly, includes gold at about 62 weight percent to about 70 weight percent, silver at about 9.0–16.0 weight percent, copper at about 7.0–18.0 weight percent, platinum at about 2.0–13.0 weight percent, palladium up to about 6.0 weight percent, nickel up to about 2.0 weight percent and zinc up to about 1.0 weight percent. Gold is a malleable metal, and the addition of copper improves formability or workability, with the resulting core more suitable for the wire drawing, cold working stages of composite filament processing. The palladium, nickel and platinum tend to increase the alloy's melting temperature. Gold is present in a proportion sufficient to provide the desired radio-opacity, despite the presence of other elements with substantially lower density and linear attenuation.

The Elgiloy alloy includes principally cobalt and chromium, and has an effective atomic number of less than thirty and a density substantially less than 0.5 pounds per cubic inch. However, the alloy is body compatible, hemo-compatible and highly resilient, with a yield strength (0.2% offset) of at least 350,000 psi, after cold working and age hardening.

Case 26 and core 24 thus cooperate to provide a prosthesis that can be viewed in vivo, and in real time. Of course, the amount of core material in relation to the amount of case material must be sufficient to insure radio-opacity while maintaining the favorable mechanical characteristics of stent 16. The area of core 24, taken along a transverse or lateral plane as illustrated in FIG. 4, should be within the range of about ten percent to sixty percent of the filament lateral cross-sectional area, i.e. the area of the combined case and core.

A suitable alternative alloy is an AuPt alloy including about 28.0–32.0 weight percent platinum, and up to 0.15 weight percent iridium, with the balance being gold. The melting temperature of this alloy is 1228° C., substantially higher than the 1063° C. melting temperature of gold.

Core 24 also can be formed of a gold alloy conveniently considered "18 karat", although the weight percent of gold is not necessarily 75.0. In particular, this alloy includes gold at about 70.0–80.0 weight percent, nickel at about 14.0–20.0 weight percent, copper at about 1.0–3.5 percent, and zinc at about 4.5–6.5 weight percent. The copper and nickel improve workability, while nickel further raises the melting temperature of the alloy and enhances work hardening to increase the strength of the core.

Another suitable 18 karat gold alloy includes gold at about 70.0–80.0 weight percent, copper at about 14.0–26.0 weight percent, and zinc at about 4.0–6.0 weight percent. The copper, once again, enhances formability. This alloy tends to be more favored for use with balloon expanded stents, while the previously discussed 18 karat gold alloy tends to be more favored for use with self-expanding stents.

Another suitable alloy is an AuNi alloy composed of up to about 5 weight percent nickel, with the balance being gold. The nickel improves formability. This alloy has a melting temperature comparable to that of gold, and accordingly composite filaments must be processed according to certain limitations (primarily lower annealing temperatures) suitable for gold cores, as is later explained.

In addition to the gold alloys just discussed, 24 karat gold, which typically is more than 99 percent pure gold, can be used as the material for core 24. As in the case of the AuNi cores, the composite filaments must be processed at lower annealing temperatures.

Other materials suitable for case 26 include other cobalt-based alloys, e.g. the Phynox and MP35N brand alloys. Cobalt-chromium and cobalt-chromium-molybdenum orthopedic type alloys also can be employed, as well as alloys of titanium-aluminum-vanadium. The MP35N alloy is widely available, and has a potential for better fatigue strength due to improved manufacturing techniques, particularly as to the vacuum melting process. The titanium-aluminum-vanadium alloys are highly biocompatible, and have more moderate stress/strain responses, i.e. lower elastic moduli.

Figure 5:
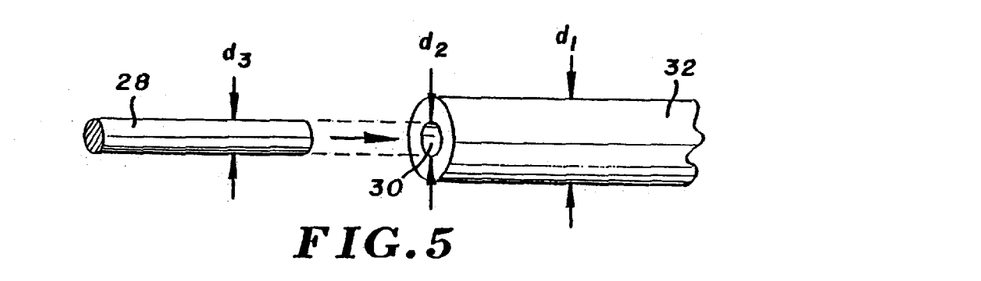
FIGS. 5, 6, 7, 8, and 9 schematically illustrate a process for manufacturing the stent.
Figure 6:
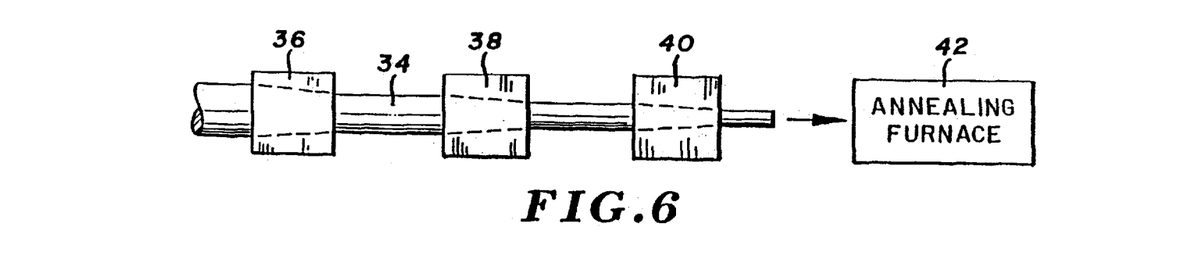
Figure 7:
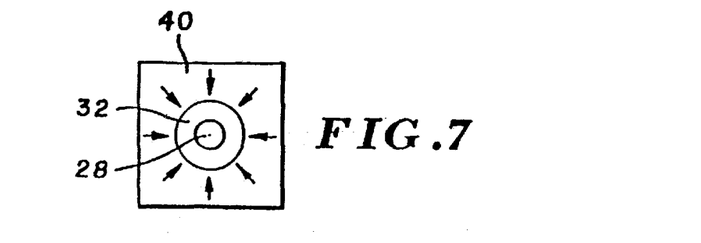

Composite filaments such as filament 18a are manufactured by a drawn filled tubing (DFT) process illustrated schematically in FIGS. 5–7. The DFT process can be performed, for example, by Fort Wayne Metals Research Products corporation of Ft. Wayne, Indiana or by Nobel-Met Ltd. of Salem, Virginia. The process begins with insertion of a solid cylinder or wire 28 of the core material into a central opening 30 of a tube 32 of the case material. Core wire 28 and tubing 32 are substantially uniform in transverse or lateral sections, i.e. sections taken perpendicular to the longitudinal or axial dimension. For example, tube 32 can have an outer diameter $d_1$ of about 0.102 inch (2.6 mm) and an inner diameter $d_2$ (diameter of opening 30) of about 0.056 inches (1.42 mm). Core or wire 28 has an outer diameter $d_3$ slightly less than the tube inner diameter, e.g. 0.046 inches (1.17 mm). In general, the wire outer diameter is sufficiently close to the tubing inner diameter to insure that core or wire 28, upon being inserted into opening 30, is substantially radially centered within the tubing. At the same time, the interior tubing diameter must exceed the core outside diameter sufficiently to facilitate insertion of the wire into an extended length of wire and tubing, e.g. at least twenty feet.

The values of the tubing inner diameter and the core outer diameter vary with the materials involved. For example, the gold alloys and platinum as compared to tantalum have a smoother exterior finish when formed into the elongate wire or core. As a result, the outer diameter of a platinum or gold alloy wire can more closely approximate the inner diameter of the tube. Thus it is to be appreciated that the optimum diameter values vary with the materials involved, and the expected length of the composite filament.

In any event, insertion of the core into the tube forms a composite filament 34, which then is directed through a series of alternating cold-working and annealing steps, as indicated schematically in FIG. 6. More particularly, composite filament 34 is drawn through three dies, indicated at 36, 38, and 40, respectively. In each of the dies, composite filament 34 is pulled through a tapered orifice, causing the case 32 and the core wire 28 to flow in a manner that reduces the filament diameter and increase the filament length.

As composite filament 34 is drawn through each die, the cold-working induces strain hardening within the filament. Accordingly, respective heating stages are provided, i.e. furnaces 42, 44 and 46, one heating stage to follow each cold-working die. At each annealing stage, composite filament 34 is heated to a temperature in the range of from about 1400° F. to about 2000° F. At each annealing stage, substantially all of the induced stresses are removed from the case and core, to permit further cold-working. Each annealing step is accomplished in a brief time, e.g. in as few as one to sixty seconds at annealing temperature, depending on the size of composite filament 34.

While FIG. 6 illustrates one cold-working stage and annealing stage, it is to be understood that the appropriate number of stages is selected in accordance with the final filament size, the desired degree of cross-sectional area reduction during the final cold-working stage, and the initial filament size prior to cold-working. In connection with composite filaments of this type, a reduction of lateral cross-sectional area in the range of about thirty percent to seventy percent is preferred, and a range of about fifty percent to sixty percent is more preferred. The range of annealing temperatures given above is appropriate for the AuAgCuPtPd gold alloy and certain other gold alloys to be discussed. It is lower than the 1700° F.–2300° F. range disclosed in the aforementioned Mayer '840 patent in connection with tantalum or platinum cores. Because of the lower annealing temperatures appropriate for its gold alloy core, filament 34 undergoes smaller reductions in diameter (lateral cross-sectional area) between annealing stages, than does the filament having a tantalum or platinum core featured in the Mayer patent.

A preferred reduction in lateral cross-sectional area during the final cold-working stage is in the range of about 52 percent to about 58 percent, and most preferably 55 percent This is in contrast to the preferred degree of reduction when tantalum or platinum is used in the core, which is 65 percent In each case, selection of the most preferred percentage of area reduction is influenced by the strength and brittleness imparted by cold working. As both of these factors increase with greater reductions of cross-sectional area, the selected area reduction results from a balance or compromise, to achieve a desired increase in strength while tolerating the accompanying reduction in ductility.

Figure 8:
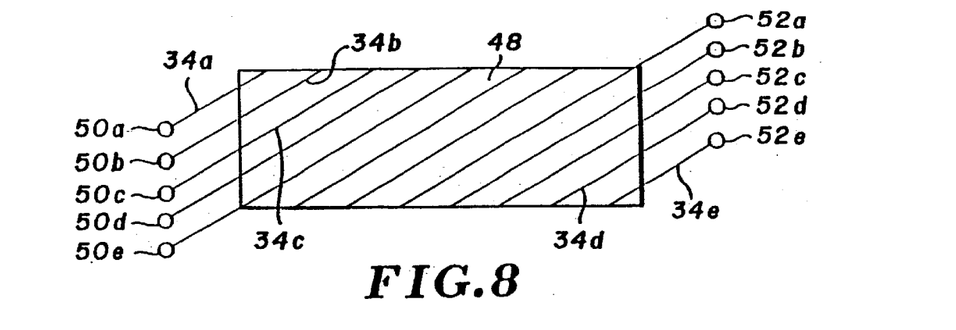

There is no annealing after the final cold-working stage. At this point, composite filament 34 is formed into the shape intended for the device incorporating the filament. In FIG. 8, several filaments or strands 34a–e are helically wound about a cylindrical form 48 and held in place at their opposite ends by sets of bobbins 50a–e and 52a–e. Strands 34a–e can be individually processed, or individual segments of a single annealed and cold-worked composite filament, cut after the final cold-working stage. In either event, the filaments cooperate to form one of the two oppositely directed sets of spaced apart and parallel filaments that form a device such as stent 16. While only one set of filaments is shown, it is to be understood that a corresponding group of filaments, helically wound and intertwined about form 48 in the opposite direction, are supported by corresponding bobbins at the opposite filament ends. In certain embodiments a paired wire construction may be utilized.

A useful prosthesis depends, in part, upon correctly supporting the filaments. The filaments are maintained in tension, and it is important to select the appropriate tensile force and apply the tensile force uniformly to all filaments. Insufficient tensile force may allow wire cast or lift effects to cause the individual filaments to depart from their helical configuration when released from the bobbins, and the braided structure of the stent may unravel.

Figure 9:
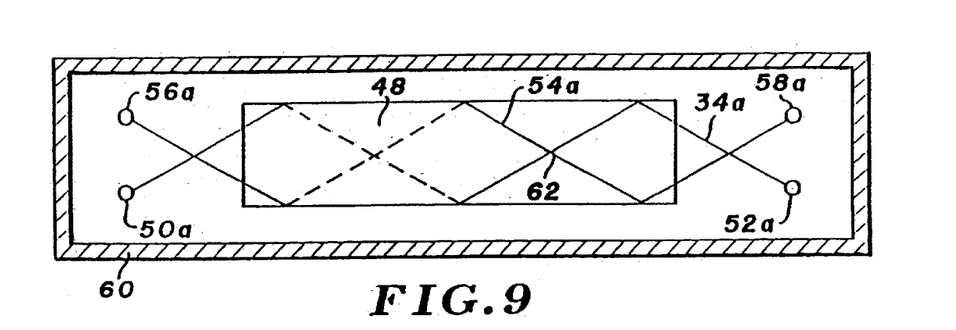

FIG. 9 illustrates two filaments 34a and 54a, one from each of the oppositely wound filament sets, supported by respective bobbins 50a/52a and 56a/58a in a furnace 60 for age hardening in a vacuum or protective atmosphere. Age hardening is accomplished at temperatures substantially lower than annealing, e.g. in the range of about 500° C.–700° C. (930° F.–1290° F.), more preferably 550° C. (1020° F.). The filaments overlie one another to form several intersections, one of which is indicated at 62. When the filaments are properly tensioned, slight impressions are formed in the overlying filament at each intersection. These impressions, or saddles, tend to positionally lock the filaments relative to one another at the intersections, maintaining the prosthesis configuration without the need for welding or other bonding of filaments at their intersections.

While only two oppositely directed filaments are illustrated as a matter of convenience, it is to be appreciated that the age hardening stage is performed after the winding and tensioning of all filaments, i.e. both oppositely directed sets. Accordingly, during age hardening, the filaments are locked relative to one another at multiple intersections. The preferred time for age hardening is about 1–5 hours, with 3 hours frequently preferred. This age hardening step is important to forming a satisfactory self-expanding prosthesis, as it substantially enhances the modulus of elasticity, yield strength, and tensile strength. Typically, the elastic modulus is increased by at least 10% and the yield strength (0.2% offset) and tensile strength are each increased by at least 20%.

Figure 10:
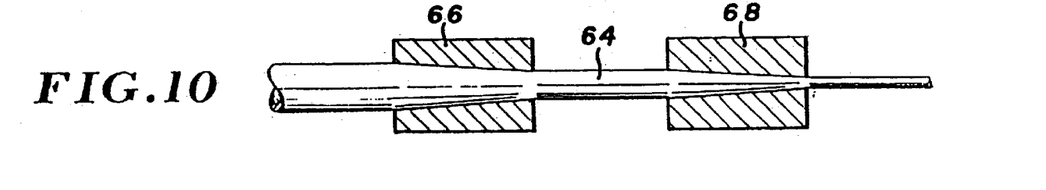
FIG. 10 schematically illustrates a swaging step of an alternative process for manufacturing the stent.

As an alternative to the process just explained, a substantially larger and shorter composite filament 64 (e.g. six inches long with a diameter of approximately ten cm) can be subjected to a series of elongation/diameter reduction steps. FIG. 10 schematically illustrates two swaging dies 66 and 68, which may be used in the course of a hot working billet reduction process. Of course, any appropriate number of swaging dies may be employed. Alternatively, the diameter reduction can be accomplished by extrusion/pulltrusion at each stage. When a sufficient number of swaging steps have reduced the composite structure diameter to about 6 millimeters (0.25 inches). The composite structure or filament can be further processed by drawing it through dies and annealing, as illustrated in FIG. 6 for the previously discussed process. As before, the composite filament is ready for selective shaping and age hardening after the final cold-working stage.

As compared to the process depicted in FIGS. 5–7, the swaging or pulltrusion approach involves substantially increased hot and cold-working of the composite structure or filament, and the initial assembling of the core into the case or shell tubing is easier. Given the much larger initial composite structure size, the structure is subjected to annealing temperatures for a substantially longer time, e.g. half an hour to an hour, as opposed to the one to fifteen second anneal times associated with the process depicted in FIG. 6. Consequently, particular care must be taken to avoid combinations of core and case materials with tendencies for intermetallic formation along the core/case interface. Further, the required hot working of the larger billet may not afford the same degree of metallurgical grain refinement.

In general, the preferred composite filaments have: (1) sufficient radio-opacity to permit in vivo viewing; (2) the preferred mechanical properties; and (3) a sufficiently low cost. The interrelationship of these factors requires that all three be taken into account in determining filament size, relationship of core 24 to case 26 as to size, and materials selected for the core and case More particularly, core 24 should be at least about 0.0015 inches in diameter, if a stent constructed of such filament is to be visible using conventional radiographic imaging equipment. At the same time, structural requirements (particularly resiliency for a self-expanding stent) require a minimum ratio of casing material with respect to core material. Thus, the visibility requirement effectively imposes a minimum diameter upon case 26 as well as core 24. Of course, appropriate selection of core and casing materials can reduce the required minimum diameters. However, potential substitute materials should be considered in view of their impact on cost—not only the material cost per se, but also as to the impact of such substitution on fabrication costs.

As noted in the Mayer '840 patent, the preferred core size, relative to the composite fiber size, varies with the filament diameter. In particular, for larger filament (diameters of 0.10–0.15 mm or 0.004–0.006 inches), sufficient radio-opacity is realized when the cross-sectional area of core 24 is about one-fourth of the cross-sectional area of the entire fiber. For smaller filaments (e.g., 0.07–0.10 mm or 0.00276–0.0039 inches) such as the type often used in stents for coronary applications), the core should contribute at least about one-third of the cross-sectional area of the composite filament. Composite filaments of this structure have core diameters in the range of 0.037–0.05 mm (0.0015–0.002 inches), with filament diameters up to about 0.135 mm or about 0.0055 inches.

The following examples illustrate formation of composite filaments according to the above-disclosed processes.

EXAMPLE 1

A composite filament having a diameter of 0.07 mm is formed from a core of the first 18 karat gold alloy discussed above, and a sheath or case of the Elgiloy cobalt-based alloy. More particularly as to this example, the gold alloy includes gold at 75.0 weight percent, nickel at 17.3 percent, copper as 2.23 percent, and zinc at 5.47 percent. The annealing between successive cold-working stages is accomplished at temperatures within the range of 870–1093° C. (1600–2000° F.). The reduction in lateral cross-sectional area of the filament, during the final cold-working (drawing) stage, is 55 percent. After the final cold-working stage, and without annealing, 18 strands of the composite filament are braided on a 4 mm diameter tubular mandrel, and the braided structure is age hardened at 550° C. for three hours. The result is a tubular mesh stent composed of 18 strands. The stent is suitable for deployment from a 5 Fr (1.7 mm) catheter into coronary arteries and pancreatic ducts in the human body.

EXAMPLE 2

A self-expanding braided tubular mesh stent is fabricated from 18 strands of a filament having the same diameter and case material as in example 1, and processed according to the same parameters. The core of the composite filament, however, is formed of the previously mentioned gold alloy composed of 62–70 weight percent gold, silver, copper, platinum, palladium, nickel, and zinc. In this example, the alloy more specifically includes gold at 63 weight percent, silver at 10 weight percent, copper at 10 weight percent, platinum at 10 weight percent, palladium at up to 6 weight percent, nickel at up to 2 weight percent, and zinc at up to 1 weight percent. Another specific version includes gold at 67 weight percent, silver at 12 weight percent, copper at 15 weight percent, platinum at 5 weight percent, palladium at up to 5 weight percent, nickel at up to 2 weight percent and zinc at up to 1 weight percent.

EXAMPLE 3

A self-expanding braided tubular mesh stent is made from 18 strands of a composite filament having the same diameter and case material as in example 1, and formed according to the process parameters outlined in example 1. The core material, however, is formed of the aforementioned AuPt alloy composed primarily of gold and including platinum at 28–32 weight percent. More particularly in this example, the alloy includes gold at 70 weight percent and platinum at 30 weight percent.

As a further variant of any one of examples 1–3, a composite filament having a diameter of 0.10 mm is formed of the same core and case materials, and cold worked and annealed according to the same parameters. Twenty strands of the filament are braided on a 6 mm diameter tubular mandrel, and age hardened for three hours at 550° C. (1022° F.). The result is a self-expanding braided tubular mesh stent suitable for deployment from a 5 Fr catheter into coronary arteries and pancreatic ducts, and further suitable for deployment from a 7 Fr (2.3 mm) catheter into the iliac arteries.

In another variant of any of examples 1–3, a 0.17 mm diameter composite filament is formed of the same sheath and core materials, and cold worked and annealed under the same conditions. Thirty strands of the composite filament are braided onto an 18 mm diameter tubular mandrel, and age hardened for three hours at 550° C. The resulting stent is suitable for deployment from a 9 Fr catheter into the tracheobronchial airways and colon.

According to another embodiment of the present invention, core 24 is composed of gold or a gold alloy with a melting point similar to that of pure gold, in lieu of the gold alloys featured in examples 1–3. The melting temperature of gold is 1063° C. (1945° F.). Thus, the range of annealing temperatures in examples 1–3 include temperatures that would cause a gold core to melt. A melting of the core would increase the likelihood of filament fracture during processing, due either to liquid metal erosion of the case material, or to a reduction in tensile strength caused by transformation of the core from a solid to a liquid. Further, any leakage of liquid alloy during annealing could damage components of the annealing furnace.

Accordingly, cold worked composite filaments with cores of gold or low melting temperature gold alloys are annealed at lower temperatures, e.g. below 1063° C. (1945° F.), and at average temperatures at most about 1055° C. (1930° F.), and more preferably within a range of 760–1038° C. (1400–1900° F.). Consequently, the reduction in filament cross-sectional area during each cold-working stage must be reduced, and the duration of each annealing stage may have to be increased. The following example illustrates formation of composite filaments in which the core is composed of a gold alloy composed primarily of gold and having a melting point similar to that of gold.

EXAMPLE 4

A composite filament having a diameter of 0.07 mm is formed with a sheath or case of Elgiloy cobalt-based alloy, and a core of a gold alloy, in particular an AuNi alloy, including nickel at 1–5 weight percent. The composite filament is annealed at temperatures within the range of 760–1038° C. The reduction in lateral cross-sectional filament area, during the final cold-working stage, is 55 percent. Eighteen strands of the filament are braided onto a 4 mm diameter tubular mandrel, and age hardened at 550° C. for three hours. The result is a self-expanding braided tubular mesh stent suitable for deployment from a 5 Fr catheter into coronary arteries and pancreatic ducts.

In a variant of example 4, a composite filament is made according to the same process parameters but has a core of pure gold.

In another variant of example 4, a composite filament having the same core and case materials, and cold worked and annealed according to the same parameters, has a diameter of 0.10 mm. Twenty strands of the resulting filament are braided on a 6 mm diameter tubular mandrel, and the structure is age hardened for three hours at 550° C. The result is a self-expanding braided tubular mesh stent suitable for deployment from a 5 Fr catheter into coronary arteries and pancreatic ducts, and suitable for deployment from a 7 Fr catheter into the iliac arteries.

A further variant of example 4 is a 0.17 mm diameter strand, formed of the same core and case materials and cold worked and annealed under the same conditions. Thirty strands of the filament are braided onto an 18 mm diameter tubular mandrel, and age hardened at 550° C. for three hours. The result is a self-expanding braided tubular mesh stent suitable for deployment from 9 Fr catheters into the tracheobronchial airways and colon.

According to further embodiments of the present invention, composite filaments have cores formed of the gold alloys of examples 1–3, and cases formed of ductile materials, e.g. tantalum or annealed stainless steel. When strands of such a filament are braided onto a mandrel as previously described, the result is a braided tubular mesh stent that is not self-expanding, but rather plastically radially compressible about a balloon catheter distal end region, in surrounding relation to a balloon. Upon desired placement of the stent, the balloon is enlargeable to radially enlarge the stent. As an alternative, the core can be formed of gold, or the aforementioned AuNi alloy.

Each of the above described composite filaments combines the desired structural stability and resiliency, with radio-opacity that allows in vivo imaging of the device composed of the filaments, during deployment and after device fixation. This result is achieved by a drawn filled tubing process that cold works a central core and its surrounding case, to positively bond the core and case together such that the composite filament behaves as a continuous, solid structure.

In accordance with the present invention, several filaments having 24 karat gold cores and Elgiloy alloy cases where fabricated by a DFT (drawn filled tubing) process, including filaments having diameters of 0.07 mm, 0.10 mm, and 0.17 mm. The filaments with diameters of 0.07 mm and 0.17 mm were tested (1) after the final annealing stage, (2) after the final coldworking stage, and (3) after age hardening. After annealing, the 0.07 mm and 0.17 mm filaments had respective ultimate tensile strengths of 130 ksi and 136 ksi, and respective elongations of 22 percent and 26 percent. After the final cold-working stage, these filaments had respective ultimate tensile strengths of 243 ksi and 208 ksi, and respective elongations of 3 percent and 4 percent. Following age hardening, these filaments had respective ultimate tensile strengths of 282 ksi and 256 ksi, and respective elongations of 2.1 percent and 2.0 percent. Further, at this stage the filaments had respective Youngs moduli of 17.5 and $17.4 \times 10^6$ psi.

The composite filaments were used to manufacture stents, all of which exhibited self-expanding behavior and no visual signs of deterioration or core melting as a result of the fabrication.

Radial compression tests were performed on the stents by squeezing them between flat and parallel platens, while preventing their longitudinal extension during compression. A 3.5 mm diameter stent formed of the 0.07 mm wires was subjected to increasing increments of radial compression, beginning at 40 percent compression. Fractured wires were found after 60 percent compression. In a 6 mm diameter stent formed of the 0.10 diameter filaments, fractured wires were observed after 50 percent compression. In a 16 mm diameter stent formed of the 0.17 mm filaments, fractured wires were observed after 80 percent compression. No fractured wires were observed in another 6 mm diameter stent formed of the 0.10 mm filaments.

In a further test, the 16 mm gold core stent and a 16 mm tantalum core stent were subjected to radial pressures. When the stents were compressed to a 15 mm diameter, the radial pressure on the gold core stent was 1256 pascals, while the radial pressure on the tantalum core stent was 1362 pascals. When the stents were compressed to a 14 mm diameter, the radial pressure on the gold core stent was 1865 pascals, and the radial pressure on the tantalum stent was 1894 pascals.

Thus, in accordance with the present invention, stents with gold and gold alloy cores are fabricated to exhibit favorable radopacity of composite filaments with tantalum and platinum cores, are less expensive to manufacture, and exhibit more favorable characteristics in connection with magnetic resonance imaging of adjacent tissue.

What is claimed is:

1. A process for manufacturing a body insertable composite filament, including:
    providing an elongate core substantially uniform in lateral cross-section and formed of a core material having a melting temperature of at least about 1600 degrees F. (870 degrees C), and an elongate tubular case substantially uniform in lateral cross-section and formed of a metal;
    inserting the core into the case to form an elongate composite filament in which the case surrounds the core;
    cold working the composite filament to reduce its outside diameter;
    annealino the composite filament after cold working, at an average annealing temperature of at most about 2000 degrees F. (1093 degrees C), and at a maximum annealing temperature less than a melting point of the core material, to substantiauly remove strain hardening and other stresses induced by said cold-working;
    further cold-working the annealed composite filament in a final cold-working stage, then forming the cold-worked filament into an intended shape; and
    while maintaining the cold-worked composite filament in the intended shape, age ardening the composite filament;
    wherein the core material is selected from the group of gold alloys consisting of:
    a. an alloy including sold at about 62–70 weight percent, silver at about 9–16 weight percent, copper at about 7–18 weight percent, and platinum at about 2–13 weight percent;
    b. an alloy including gold from about 60 weight percent to about 99 weight percent, silver, copper, platinum, and at least one further metal from the group consisting of palladium, nickel, and zinc;
    c. an alloy including gold at about 70–80 weight percent, copper at about 14–26 weight percent, and zinc at about 4–6 weight percent;
    d. an alloy containing gold at about 70–80 percent, copper at about 1–3.5 percent, zinc at about 4.5–6.5 percent, and nickel at 14–20 percent; and
    e. an alloy consisting essentially of gold from about 60 weight percent to about 99 weight percent, and nickel.

2. The process of claim 1 wherein:
the alloy further includes iridium.

3. The process of claim 1 wherein:
said providing an elongate tubular case comprises forming the case from a cobalt-based alloy.

4. The process of claim 3 wherein:
the cobalt-based alloy includes chromium.

5. The process of claim 4 wherein:
the cobalt-based alloy further includes iron, nickel, and molybdenum.

6. The process of claim 1 wherein:
said providing an elongate tubular case comprises forming the case of a case material selected from the group consisting of tantalum and annealed stainless steel.

7. The process of claim 1 wherein:
said cold working the annealed composite filament in the final cold-working stage comprises reducing a lateral cross-sectional area of the composite filament by about 52 to 58 percent.

8. The process of claim 7 wherein:
said lateral cross-sectional area is reduced during said final cold-working stage by about 55 percent.

9. The process of claim 1 wherein:
the age hardening of the composite filament comprises maintaining the filament at a temperature within the range of 500–700 degrees C.

10. The process of claim 9 wherein:
said age hardening comprises maintaining the composite filament at a temperature of about 550 degrees C.

11. The process of claim 9 further including:
maintaining the cold-worked composite filament in tension during said age hardening.

12. The process of claim 1 wherein:
said annealing comprises maintaining the composite filament at an average annealing temperature within the range of 1400–1900 degrees F. (760–1038 degrees C).

13. The process of claim 1 wherein:
said annealing comprises maintaining the composite filament at an average annealing temperature in the range of 1400–2000 degrees F. (760–1093 degrees C).

14. The process of claim 1 wherein:
the elongate core is cylindrical.

15. A process for manufacturing a body insertable composite filament with a core formed of gold or a gold alloy, including:
providing an elongate core substantially uniform in lateral cross-section and consisting essentially of a core material selected from the group consisting of gold and gold alloys, and further providing an elongate tubular case substantially uniform in lateral cross-section and formed of a metal selected from the group consisting of tantalum and annealed stainless steel;
inserting the core into the case to form an elongate composite filament in which the case surrounds the core;
cold-working the composite filament to reduce its outside diameter;
annealing the composite filament after cold-working, at a temperature within the range of 760–1038 degrees C. (1400–1900 degrees F.) to substantially remove strain hardening and other stresses induced by cold-working;
further cold-working the annealed composite filament in a final cold-working stage, reducing a lateral cross-sectional area of the composite filament by about 52–58 percent; and
after said final cold-working stage, age hardening the composite filament.

16. The process of claim 15 further including:
maintaining the cold-worked composite filament in an intended shape during said age hardening.

17. The process of claim 15 further including:
selecting, as the core material, a gold alloy containing from about 60 weight percent to about 99 weight percent gold, with a melting temperature of at least about 1600 degrees F. (870 degrees C.).

18. The process of claim 15 further including:
selecting the core material from the group of gold alloys consisting of:
a. an alloy containing gold, silver, copper, and platinum;
b. an alloy containing gold, copper, and zinc;
c. an alloy containing gold and platinum; and
d. an alloy containing gold and nickel.

19. The process of claim 15 wherein:
said lateral cross-sectional area is reduced during said final cold-working stage by about 55 percent.

20. The process of claim 15 wherein:
the elongate core is cylindrical.

21. A process for manufacturing a body insertable composite filament, including:
providing an elongate core substantially uniform in lateral cross-section and formed of a core material consisting essentially of a core material selected from the group consisting of gold and gold alloys, said core having a melting temperature of at least about 1600 degrees F. (870 degrees C); and an elongate tubular case substantially uniform in lateral cross-section and formed of a metal selected from the group consisting of tantalum and annealed stainless steel;
inserting the core into the case to form an elongate composite filament in which the case surrounds the core;
cold working the composite filament to reduce its outside diameter;
annealing the composite filament after cold working, at an average annealing temperature of at most about 2000 degrees F. (1093 degrees C), and at a maximum annealing temperature less than a melting point of the core material, to substantially remove strain hardening and other stresses induced by said cold-working;
further cold-working the annealed composite filament in a final cold-working stage, then forming the cold-worked filament into an intended shape; and
while maintaining the cold-worked composite filament in the intended shape, age hardening the composite filament.

22. The process of claim 21 wherein:
said providing an elongate core comprises selecting as the core material a gold alloy containing from about 60 weight percent to about 99 weight percent gold.

23. The process of claim 22 wherein:
said gold alloy is selected from the group consisting of: an alloy containing old, silver, copper, and platinum; an alloy containing gold, copper, and zinc; an alloy containing gold and platinum; and an alloy containing gold and nickel.

24. The process of claim 21 wherein:
the age hardening of the composite filament comprises maintaining the filament at a temperature within the range of 500–700 degrees C.

25. The process of claim 21 further including:
maintaining the cold-work ed composite filament in tension during said age hardening.

26. A process for manufacturing a body insertable composite filament, including:
providing an elongate core substantially uniform in lateral cross-section and formed of a core material consisting essentially of a core material selected from the group consisting of gold and gold alloys, said core having a melting temperature of at least about 1600 degrees F. (870 degrees C); and an elongate tubular case substantially uniform in lateral cross-section and formed of a metal;
inserting the core into the case to form an elongate composite filament in which the case surrounds the core;
cold working the composite filament to reduce its outside diameter;
annealing the composite filament after cold working, at an average annealing temperature of at most about 2000 degrees F. (1093 degrees C), and at a maximum annealing temperature less than a melting point of the core material, to substantially remove strain hardening and other stresses induced by said cold-working;
further cold-working the annealed composite filament in a final cold-working stage, then forming the cold-worked filament into an intended shape; and
while maintaining the cold-worked composite filament in the intended shape, age hardening the composite filament at a temperature of about 550 degrees C.

27. The process of claim 26 wherein:
said providing an elongate core comprises selecting as the core material a gold alloy containing from about 60 weight percent to about 99 weight percent gold.

28. The process of claim 27 wherein:
said gold alloy is selected from the group consisting of: an alloy containing gold, silver, copper, and platinum; an alloy containing gold, copper, and zinc; an alloy containing gold and platinum; and an alloy containing gold and nickel.

29. The process of claim 27 further including:

maintaining the cold-worked composite filament in tension during said age hardening.

30. A process for manufacturing a body insertable composite filament with a core formed of gold or a gold alloy, including:

providing an elongate core substantially uniform in lateral cross-section and consisting essentially of a core material selected from the group consisting of gold and gold alloys, and further providing an elongate tubular case substantially uniform in lateral cross-section and formed of a metal;

inserting the core into the case to form an elongate composite filament in which the case surrounds the core;

cold-working the composite filament to reduce its outside diameter;

annealing the composite filament after cold-working, at a temperature within the range of 760–1038 degrees C. (1400–1900 degrees F.) to substantially remove strain hardening and other stresses induced by cold-working;

further cold-working the annealed composite filament in a final cold-working stage, reducing a lateral cross-sectional area of the composite filament by about 52–58 percent; and after said final cold-working stage, age hardening the composite filament at a temperature of about 550 degrees C.

31. The process of claim 30 further including:

maintaining the cold-worked composite filament in an intended shape during said age hardening.

32. The process of claim 30 further including:

selecting, as the core material, gold alloy containing from about 60 weight percent to about 99 weight percent gold.

* * * * *